(12) United States Patent
Rushforth

(10) Patent No.: US 7,091,246 B2
(45) Date of Patent: Aug. 15, 2006

(54) DIETARY SUPPLEMENTATION WITH STOICHIOMETRICALLY SPECIFIC POTASSIUM MAGNESIUM CITRATE

(75) Inventor: Dennis S. Rushforth, San Antonio, TX (US)

(73) Assignee: Mission Pharmacal Co., San Antonio, TX (US)

( * ) Notice: Subject to any disclaimer, the term of this patent is extended or adjusted under 35 U.S.C. 154(b) by 305 days.

(21) Appl. No.: 10/797,321

(22) Filed: Mar. 8, 2004

(65) Prior Publication Data

US 2005/0197402 A1  Sep. 8, 2005

(51) Int. Cl.
*A61K 31/19* (2006.01)
*C07C 59/265* (2006.01)

(52) U.S. Cl. ........................... 514/574; 562/584

(58) Field of Classification Search .................. None
See application file for complete search history.

(56) References Cited

U.S. PATENT DOCUMENTS

| | | | |
|---|---|---|---|
| 4,895,980 A | 1/1990 | Walsdorf et al. |
| 4,985,593 A | 1/1991 | Walsdorf et al. |
| 5,219,889 A | 6/1993 | Walsdorf et al. |
| 5,432,200 A | 7/1995 | Walsdorf et al. |
| 6,514,537 B1 | 2/2003 | Murphy |

OTHER PUBLICATIONS

Remington's Pharmaceutical Sciences, 16th edition, published 1980 by Mack Publishing Co. (PA), pp. 1535-1539.*

* cited by examiner

*Primary Examiner*—Raymond J. Henley, III
(74) *Attorney, Agent, or Firm*—Fulbright & Jaworski LLP

(57) ABSTRACT

A specific form of a dual mineral salt having potassium, magnesium, and citrate in a stoichiometric ratio of potassium:magnesium of less than 4:1 is disclosed. Methods of making the composition and using the composition as a dietary supplement are also disclosed.

20 Claims, 16 Drawing Sheets

DIETARY SUPPLEMENTATION WITH STOICHIOMETRICALLY SPECIFIC POTASSIUM MAGNESIUM CITRATE

TECHNICAL FIELD

The invention relates to a new composition of matter comprising, potassium, magnesium and citrate in a single compound in which the stoichiometric ratio of potassium to magnesium is less than 4:1. One aspect of the invention relates to the novel composition of the invention, and its method of synthesis. Another aspect of the invention relates to the use of the composition as a dietary supplement. Another aspect of the invention relates the method of manufacturing tablets from such salt. Still another aspect of the invention relates to a novel method for more effectively supplementing dietary magnesium and potassium by administering magnesium, potassium and citrate in a single salt.

BACKGROUND OF THE INVENTION

The use of magnesium and potassium salts for dietary supplementation is well known. One useful composition for such supplementation is potassium magnesium citrate (PMC). Unfortunately, early compositions of PMC exhibited poor processing and poor thermal stability. It is desirable to have a new PMC composition suitable for dietary supplementation that possesses superior processing and thermal stability.

A typical reaction for the production of tetra potassium magnesium dicitrate involves both the magnesium and potassium carbonates according to the reaction:

$$10K_2CO_3 + (MgCO_3)_4Mg(OH)_2 \cdot 5H_2O + 10H_3(C_6H_2O_7)$$
$$\rightarrow 5K_4Mg(C_6H_5O_7) + 21H_2O + 14CO_2$$

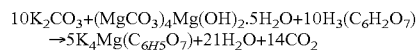

Magnesium Carbonate USP is more correctly identified as magnesium carbonate magnesium hydroxide and its correct stoichiometric formula is shown in the above reaction equation. In practice, the reaction seems to go as predicted. The carbonates and hydroxides react with citric acid producing a material with the empirical formula of $K_4Mg(C_6H_5O_7)_2$ plus carbon dioxide and water.

A number of these problems were addressed with the introduction of dual mineral salts of potassium, magnesium, and citrate. In U.S. Pat. No. 4,985,593, Walsdorf et al., described to a new composition of matter comprising magnesium, potassium and citrate in a single compound which allowed for effectively supplementing dietary magnesium and potassium by administering magnesium, potassium and citrate in a single salt. U.S. Pat. No. 4,895,980, also to Walsdorf, disclosed methods of making that aforementioned composition. Finally, U.S. Pat. No. 5,219,889 to Walsdorf et al., disclosed methods of supplementing dietary potassium, magnesium, and citrate by oral administration in which the ratio of potassium:magnesium:citrate is 4:1:2.

While the Walsdorf and other compositions addressed many of the earlier problems in the area of potassium and magnesium dietary supplementation, some problems remained. Improved processing, in addition to decreasing production costs, are expected to result in potentially new formulations and finished product dosage forms, which can improve shelf stability of the finished product. Additionally, improved thermal stability of the dietary supplement is desirable.

Earlier compositions of PMC targeted a ratio of K:Mg: Citrate of 4:1:2 but there was little control over the resulting compound. The result was a salt or mixture having a potassium:magnesium:citrate ratio near to 4:1:2 in which neither the completeness of reaction nor the final stoichiometry of the resulting compound was adequately determined. This resulted in batches of PMC that had differing properties including varied thermal stability, final stoichiometry and processability. The present invention discloses a pure PMC which possesses a precisely defined stoichiometry whereby stoichiometry is precisely controlled by process conditions. The present invention also encompasses a process for making the new composition. The resulting composition is useful as a dietary supplement yet does not suffer from the deficiencies of the earlier compositions.

To this end, a new composition of potassium magnesium citrate has been made which exhibits enhanced thermal stability and is more amenable to analytical quality control monitoring. These advantages are realized while preserving the usefulness as a dietary supplement enjoyed by earlier compositions.

BRIEF SUMMARY OF THE INVENTION

The present invention is directed to a composition, method of making the composition and a method of using the composition as a dietary supplement. The following numbered sentences provide non-limiting examples of the present invention.

In the present invention there is a composition comprising a salt of potassium, magnesium, and citrate having the general formula $K_xMg_y(C_6H_5O_7)_z$, wherein z is 2, and x is greater than or equal to 3.7 and less than 4.0 and y is greater than or equal to 1.0 and less than 1.15, and wherein electroneutrality is preserved by adjusting x and y so that x+2y is equal to 6 or by including ions other than potassium, magnesium, or citrate. In one embodiment, the ions other than potassium, magnesium, or citrate are hydrogen ions. In another embodiment, x is greater than or equal to 3.8 and less than or equal to 3.95. In one embodiment, the salt, in its modulated differential scanning calorimetry thermogram, has an endothermic peak for decomposition comprising an onset temperature of greater than 320° C., a peak minimum temperature of greater than 327° C., and a peak width of less than 9° C.

In another aspect of the present invention, there is a pharmaceutical composition useful as a magnesium and potassium dietary supplement, the composition comprising magnesium potassium citrate as a single salt, the salt having the general formula $K_xMg_y(C_6H_5O_7)_z$, wherein z is 2, and x is greater than or equal to 3.7 and less than 4.0 and y is greater than or equal to 1.0 and less than 1.15, and wherein electroneutrality is preserved by adjusting x and y so that x+2y is equal to 6, or including ions other than potassium, magnesium, or citrate. In one embodiment, the ions other than potassium, magnesium, or citrate are hydrogen ions. In one embodiment, the ratio of potassium ion to magnesium ion is less than or equal to 3.95:1 and greater than or equal to 3.8:1. In another embodiment, the salt, in its modulated differential scanning calorimetry thermogram, has an endothermic peak for decomposition comprising an onset temperature of greater than 320° C., a peak minimum temperature of greater than 327° C. and, a peak width of less than 9° C.

In another aspect of the present invention, there is a method for producing a magnesium potassium citrate composition comprising the steps of mixing citric acid and water with uninterrupted agitation; while still agitating, gradually adding a magnesium compound and a potassium compound thereto in such proportions that the mixture thus formed comprises potassium ions, magnesium ions, and citrate ions and has the general formula $K_xMg_y(C_6H_5O_7)_z$, wherein z is 2, and x is greater than or equal to 3.7 and less than 4.0 and y is greater than or equal to 1.0 and less than 1.15, and wherein electroneutrality is preserved by adjusting x and y so that x+2y is equal to 6 or, including ions other than potassium, magnesium, or citrate; blending the resultant composition; and thereafter, drying and milling the resultant composition to form a magnesium potassium citrate composition. In one embodiment, the water content of the reaction mixture is at least 120% by weight relative to theoretical dry yield of potassium magnesium citrate. In another embodiment, the drying step comprises spray drying. In another embodiment, the method further comprises the step of exposing the reaction mixture to heat, pressure, humidity, or any combination thereof. In one embodiment, the water content of the reaction mixture is about 50% by weight relative to theoretical dry yield of potassium magnesium citrate. In one embodiment, the magnesium compound is selected from the group consisting of magnesium carbonate, magnesium citrate, magnesium oxide, and magnesium hydroxide. In one embodiment, the potassium compound is selected from the group consisting of potassium carbonate, potassium citrate, potassium bicarbonate, and potassium hydroxide. In one embodiment of the method, the composition has an endothermic peak for decomposition in its modulated differential scanning calorimetry thermogram, said peak comprising an onset temperature of greater than 320° C., a peak minimum temperature of greater than 327° C., and a peak width of less than 9° C.

In another aspect of the present invention, there is a method for supplementing dietary potassium and magnesium comprising administering to a person or animal, potassium magnesium citrate in a single salt consisting essentially of potassium, magnesium and citrate ions and has the general formula $K_xMg_y(C_6H_5O_7)_z$, wherein z is 2, and x is greater than or equal to 3.7 and less than 4.0 and y is greater than or equal to 1.0 and less than 1.15, and wherein electroneutrality is preserved by adjusting x and y so that x+2y is equal to 6 or, including ions other than potassium, magnesium, or citrate. In one embodiment, the step of administering comprises orally administering. In another embodiment, the step of orally administering comprises orally administering tablets. In another embodiment of the method, the said salt has an endothermic peak for decomposition in its modulated differential scanning calorimetry thermogram, the peak comprising an onset temperature of greater than 320° C.; a peak minimum temperature of greater than 327° C.; and a peak width of less than 9° C.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
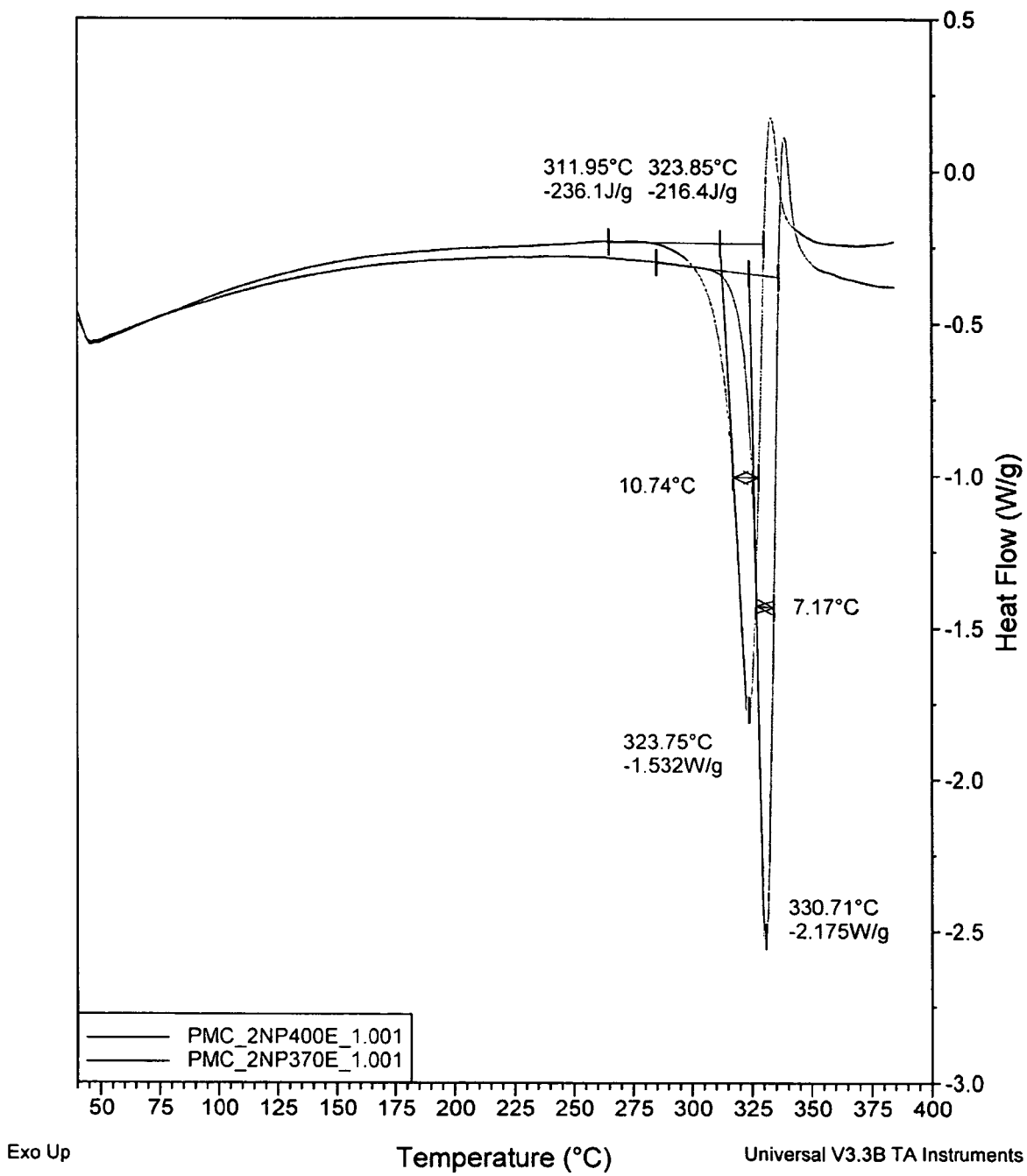
FIG. 1. DSC curves for two different PMC batches.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," and "comprising" are interchangeable and one of skill in the art is cognizant that these terms are open ended terms.

A new compound, a dual mineral salt, has now been synthesized by reacting controlled quantities of citric acid, a magnesium compound and a potassium compound, preferably as follows:

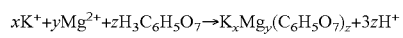

$$xK^+ + yMg^{2+} + zH_3C_6H_5O_7 \rightarrow K_xMg_y(C_6H_5O_7)_z + 3zH^+$$

wherein x is less than 4.0, y is about 1, and z is about 2. Electroneutrality is preserved by low levels of ions other than potassium, magnesium, or citrate. Preferably, these are hydrogen ions. Alternatively, electroneutrality may be preserved by additional magnesium to account for the lesser charge contribution of the decreased potassium; in this case, although x is less than 4.0, x and y are adjusted such that x+2y is equal to six. Preferably, the ratio of potassium ions to magnesium ions is less than or equal to 3.95:1 and greater than or equal to 3.8:1.

Alternatively, the same compound can be synthesized by reacting controlled quantities of potassium citrate, magnesium and, in certain cases, small amounts of citric acid as follows:

$$(x/3)K_3(C_6H_5O_7)+(y/3)Mg_3(C_6H_5O_7)_2+(v/3)H_3(C_6H_5O_7) \rightarrow K_xMg_y(C_6H_5O_7)_z+vH^+$$

wherein x is less than 4.0, y is about 1.0 or greater and $(x/3+2y/3+v/3)=z$ and is about 2. Preferably the mole ratio of potassium ions to magnesium ions is less than or equal to 3.95:1 and greater than or equal to 3.8:1.

The reaction is preferably initiated by the slow addition of the magnesium compound to a mixture of water and citric acid, followed by the slow introduction of the potassium compound to the reaction mixture. The reactants are added according to the stoichiometric quantities described in the reaction above.

The magnesium compound is preferably selected from the group consisting of magnesium carbonate, magnesium oxide and magnesium hydroxide. Magnesium carbonate is the preferred magnesium compound although the use of other magnesium salts is possible. The potassium compound is preferably selected from the group consisting of potassium carbonate and potassium bicarbonate, with potassium carbonate being generally preferred because of its lower cost.

The citric acid is mixed with water with uninterrupted agitation, and the magnesium compound and potassium compound are thereafter sequentially mixed with the citric acid. This dense hydrated mixture comprises potassium ions, magnesium ions and citrate ions in a proportion of about x:y:z wherein x is less than 4.0, y is about 1, and z is about 2. electroneutrality is preserved by adjusting x and y so that x+2y is 6; or, including ions other than potassium, magnesium, or citrate. Preferably, when ions other than potassium, magnesium, or citrate are included, these ions are hydrogen ions.

There are four reaction schemes that can be used to describe preferred ways to produce potassium magnesium citrate. In schemes labeled "complete", there is no leftover citric acid nor potassium carbonate. In schemes labeled "limited," not all of the starting materials can completely react. There is either too little or too much of the potassium carbonate. Either potassium carbonate or tetrahydrogen magnesium dicitrate is the limiting reagent. The labels also indicate the starting materials. Schemes labeled "carbonate" use potassium carbonate, magnesium carbonate and citric acid as the starting materials. Schemes labeled "citrate" use potassium citrate and magnesium citrate as the starting materials.

Reaction Scheme 1: Complete Carbonate $$(k/2)K_2(CO_3) + (m/5)(MgCO_3))4(Mg(OH)_2)\cdot 5H_2O + 2H_3(C_6H_5O_7)$$

$$\downarrow$$

$$K_kMg_m(C_6H_5O_7)_2 + (k/2 + 4m/5 + 2m/5 + 2m)H_2O + (k/2 + 4m/5)CO_3$$

Reaction Scheme2: Complete Citrate $$(k/3)\ K_3(C_6H_5O_7)\ +\ (m/3)\ Mg_3(C_6H_5O_7)_2 \longrightarrow$$
$$K_kMg_m(C_6H_5O_7)_2 \quad k+2m=6\ or\ m=(6-k)/2$$

While the above complete reactions are theoretically simple, in practice there are difficulties achieving them. For example, potassium carbonate is hygroscopic and can absorb water. The generalized reaction to account for either limited or excess potassium carbonate is.

Reaction Scheme 3: Limited Carbonate $$(k/2)K_2(CO_3) + (m/5)(MgCO_3))4(Mg(OH)_2)5H_2O + 2H_3(C_6H_5O_7)$$

$$\downarrow$$

$$K_kH_hMg_m(C_6H_5O_7)_2(CO_3)_c + (k/2 + 4m/5 + 2m/5 + m)H_2O + (k/2 + 4m/5)CO_3$$

where h=4−k if k<4 and 0 if k≧4 and c=k−4 if k>4 and 0 if k≦4.

The product of the limited carbonate scheme, $K_kH_hMg_m(C_6H_5O_7)_2(CO_3)_c$, can also be made from potassium citrate, magnesium citrate with the addition of citric acid or potassium carbonate according to the following reaction.

Reaction Scheme 4: Limited Citrate $$(k/3)K_3(C_6H_5O_7) + (m/3)Mg_3(C_6H_5O_7)_2 +$$
$$(h/3)H_3(C_6H_5O_7) + cK_2CO_3 \longrightarrow K_{(k+2c)}H_hMg_m(C_6H_5O_7)_2(CO_3)_c$$

where h=4−k if k<4 and 0 if k≧4 and c=k−4 if k>4 and) if k≦4.

During addition of the magnesium compound, the temperature of the mixture is desirably controlled below about 100° C. by controlling the rate of addition. If the temperature of the reaction mixture is permitted to rise above about 120° C., product degradation may occur. A preferred temperature for the reaction mixture during and following addition of the magnesium compound is about 80° C.

The hydrated reaction mixture preferably has a water content at least 30 weight percent of the expected dry yield and preferably about 50 weight percent. When the water content of the reaction mixture is 120% of the expected yield of potassium magnesium citrate, the salt is completely dissolved and the resultant composition is amenable to spray drying.

The compositions of the present invention are those magnesium potassium citrate compositions comprising a potassium:magnesium:citrate molar composition of x:y:z wherein y is 1, z is 2, and x is within the range 3.7≦x≦4.0. A preferred embodiment of the magnesium potassium citrate composition of the invention comprises a potassium:magnesium:citrate molar composition wherein y is 1, z is 2, and x is within the range 3.7≦x≦3.95. Finished dosage forms, such as tablets, are then manufactured using various formulations of the compositions. As a non-limiting example, non-wax matrix tablets of the composition, characteristically have a density of about 1.7 g/cc and wax matrix tablets have a density of about 1.5 g/cc are preferred. For aesthetic or other purposes, these tablets may be coated by conventional means with mixtures comprising substances such as sugar, polyvinylpyrrolidone, calcium carbonate and titanium oxide, or the like.

The process most commonly used consists of dissolving the citric acid in water and then adding the magnesium carbonate gradually while stirring. When the reaction is complete, potassium carbonate is added incrementally (being careful that the mixture does not foam out of the mixing vessel).

Complete mixing is preferred. Batches may be made in beakers by stirring with a spatula and with magnetic stirrers. Small batches have been made using a KitchenAid® mixer. Larger batches have been made using paddle mixers, ribbon mixers, plow mixers, and even a counter motion mixer. Mixing results were varied. Of all the mixers on a large scale, the plow mixer has proven to be the most efficient. Batches in other mixers require more water to achieve a complete reaction than is required in a plow mixer.

Because the amount of water used to facilitate the reaction is such a critical part of the process, the process is more easily discussed focusing on water content. Batches made with only a small amount of water (10%–30% of the theoretical PMC yield) are not made reproducibly and often the reagents are not completely reacted. Batches made with more water (greater than 40% of the theoretical yield) react completely and the order of addition does not seem to be important, other than, perhaps, affecting the ease of controlling the reaction.

Low Water Content Batches

Batches with only a small amount of water are difficult to make in beakers and are preferably made in ribbon mixers. When calcium carbonate and citric acid are reacted in a limited amount of water, the reaction mass foams and then forms a soup. Then quickly it converts from a soup to a sticky mass and is converted to granules. With PMC, this granulation does not always happen. Before it granulates, PMC forms a sticky phase which, instead of quickly forming granules, more often forms large balls and lumps. When granulation does occur, often the reaction is incomplete. In these low water content batches mixing is very important. Batches made in a plow mixer are more likely to be completely reacted than those made in a ribbon mixer with the same amount of water. All reaction mixture water content values herein are expressed as a percentage of theoretical dry yield of potassium magnesium citrate. At 30%–40% water (based on theoretical dry yield) the materials seem adequately mixed and the reaction goes to completion in plow mixers.

50% Water Batches

Batches made with 50% water with respect to the theoretical PMC yield are useful because they allow the visual monitoring of reaction completion. After the magnesium carbonate is added, the reaction proceeds with effervescence. When the reaction is complete, the effervescence stops and a clear light yellow solution remains. Likewise, when the potassium carbonate is added, the reaction continues with effervescence for some time. When that reaction is complete, the effervescence stops and a clear light yellow solution remains. Within minutes of the cessation of effervescence, the clear solution clouds and, if stirring continues, a white paste forms. The viscosity increases with the length of time stirred. Samples have been divided, placed on aluminum drying pans, and dried at different temperatures. In each case, a hard ceramic-like disk forms.

100% Water Batches

PMC batches made with water at 100% of theoretical yield react similarly to the 50% water batches. After the reaction is complete, it takes much more time before the solution clouds. PMC is very soluble and, at this level of water, most of the PMC is dissolved and remains in solution but there is a small amount precipitate that forms. With rapid stirring for a long time, much of the water is incorporated into a flowing suspension or light paste. When allowed to set over 24 hours or more, the sample separates into a paste on the bottom of the container and a clear solution on top.

Once the potassium magnesium citrate is made, it must be dried. Small quantities are easily dried on trays in lab ovens to the anhydrous material. Drying at room temperature, even small samples, takes several days to get to, approximately, a hemihydrate. Material dried at 150° C. may appear more yellow or light brown but does not seem to vary significantly in terms of DSC analysis.

120% Water Batches

PMC batches made with water at 120% or more of theoretical yield results in complete dissolution of the salt in the mixture. PMC is very soluble and, at this level of water, all of the PMC is dissolved and remains in solution. Upon dying, the PMC of the present invention can form more than one polymorph, all of which are useful and are part of the present invention. It has been found specifically that spray drying under certain conditions favors the formation of one specific polymorph identifiable by DSC.

Analytical Methods

Potassium Magnesium Citrate has been studied using many analytical techniques. Sold State Nuclear Magnetic Resonance, Fourier Transform Infrared Spectroscopy (FTIR), Fourier Transform Near-Infrared Spectroscopy (NIR), and Powder X-Ray Diffraction (PXRD) have been used to characterize the materials formed. The most powerful technique for observing important differences in these materials has been Differential Scanning Calorimetry (DSC). To a lesser degree, Thermal Gravimetric Analysis (TGA) has also proven useful. Assay determinations have been done by atomic absorption spectroscopy, titrimetric assay, and calorimetric assay, but ion chromatography proved to be the most useful.

Results of analytical testing demonstrate that the PMC formed is a stable compound, distinguishable from mixtures of potassium citrate and magnesium citrate. All the results from the various techniques support this conclusion. The Solid State Nuclear Magnetic Resonance (SSNMR) spectrum of PMC was radically different from that of either potassium citrate or magnesium citrate or a blend of potassium citrate and magnesium citrate. The Near-infrared NIR) spectrometer could distinguish between a stoichiometric blend of potassium citrate and magnesium citrate. PXRD patterns showed that the structure of PMC was easily distinguishable from that of potassium citrate, magnesium citrate or a stoichiometric blend. The thermograms from DSC were compelling. PMC decomposed at a temperature higher than that of potassium citrate or magnesium citrate. Using DSC, it was possible to detect adulteration of PMC with a stoichiometric blend of potassium citrate and magnesium citrate at 1 or 2%.

DSC Curves

Differential Scanning Calorimetry (DSC) measures heat flow as a function of time or temperature and is used to study material transformation whether they be physical, such as phase changes, or chemical, such as decomposition. There are several parameters that can be obtained from a DSC thermogram. In the present work, the focus was on the onset temperature, the temperature of the peak minimum, and the peak width. DSC information is useful in understanding the purity and nature of material. For example, when a pure crystalline substance melts, the melting point is sharp. In DSC, that sharpness is shown by a narrow melting peak in the thermogram. If there are impurities or defects in the crystalline nature, the melting takes place at lower temperatures and over a larger range of temperatures. In DSC, the impurities are shown by a lower onset temperature and peak temperature, and a broader peak in the thermogram. When there are discrete impurities, they can melt at their melting points. In DSC, discrete impurities can be shown by additional peaks in the thermogram.

For PMC, the transformation of major interest is decomposition. While a decomposition curve is usually broader and can be more complicated, some of the same phenomena are seen as with melting. Impurities and defects will cause broader and lower temperature peaks. Discrete impurities can show their own decomposition peaks.

FIG. 1 shows modulated DSC curves or thermograms for two different PMC batches. These were made at slightly different stoichiometries. The onset temperature, the temperature at peak minimum, and the peak width are labeled.

Figure 2:
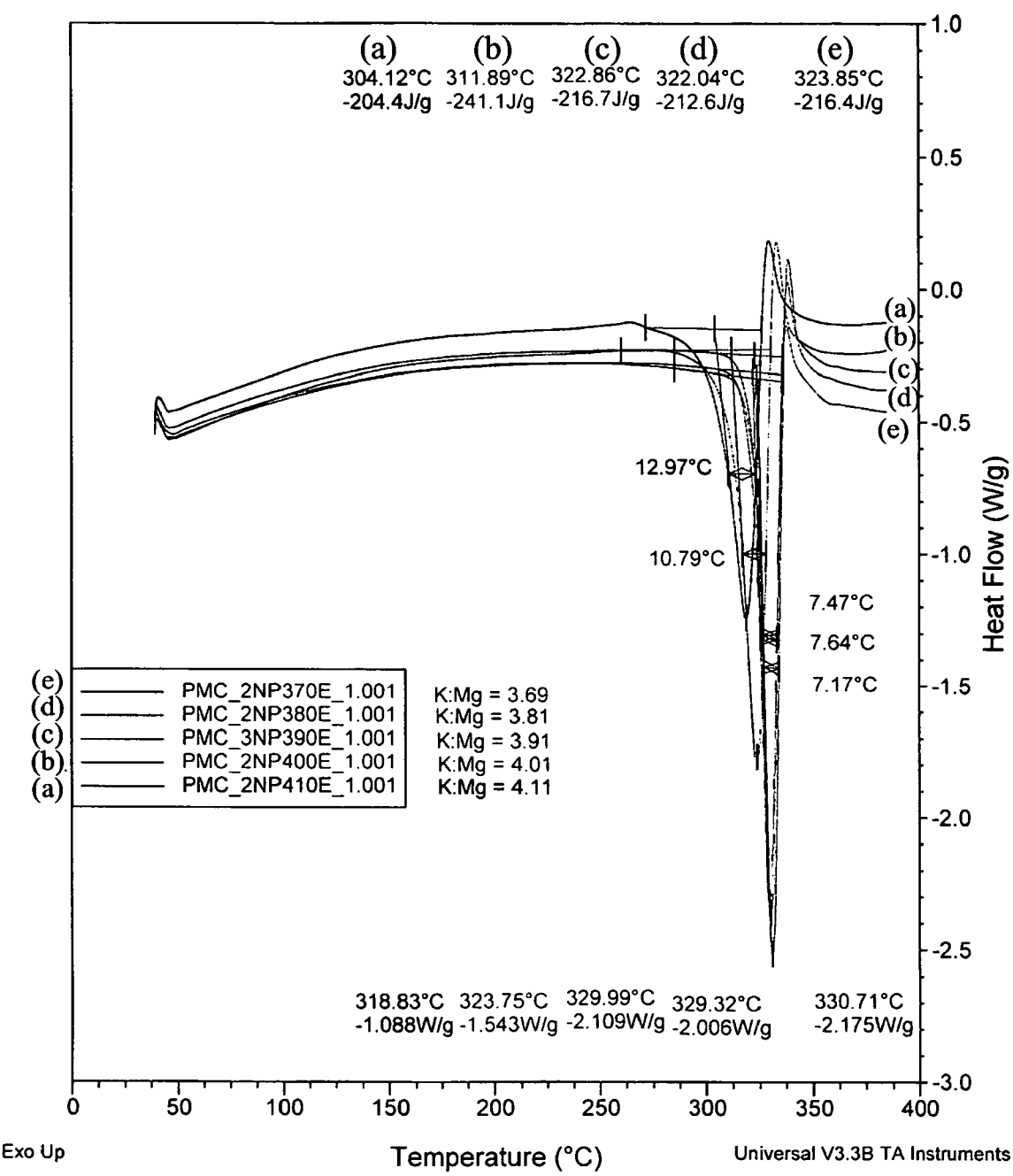
FIG. 2. DSC curves for PMC having different K:Mg ratios.
Figure 3:
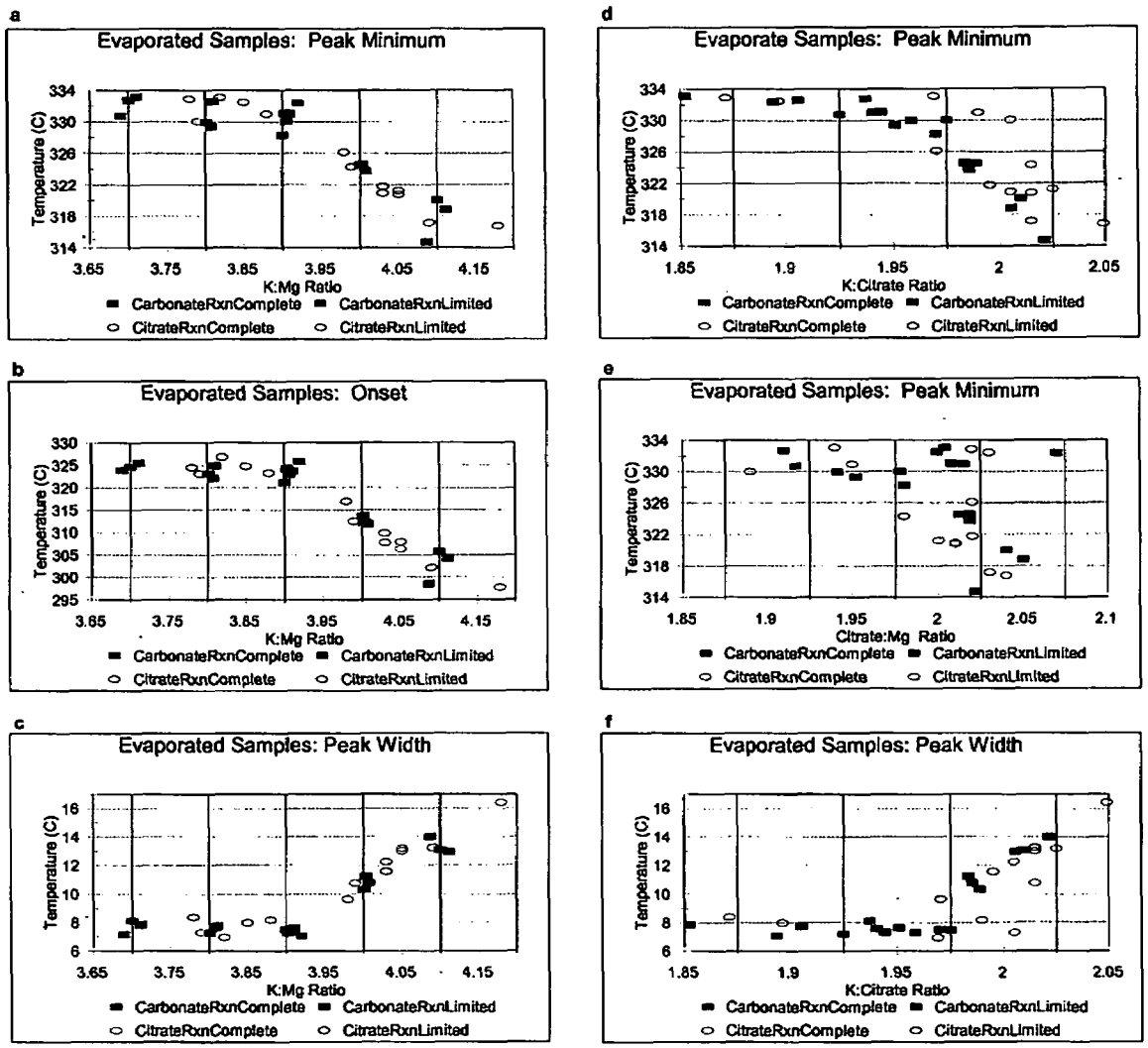
FIG. 3. DSC Peak Parameter vs. composition for PMC.

The DSC results demonstrated a dependency on the potassium-to-magnesium ratio. The samples in the precipitation study that were prepared by evaporation show the same trends. FIG. 2 shows some of the modulated DSC curves and FIGS. 3a–3f show some of the parameters determined from those DSC curves plotted as a function of the measured potassium-to-magnesium ratio, the potassium-to-citrate ratio, and the magnesium-to-citrate ratio. The parameter that appears to correlate best is the potassium-to-magnesium ratio. Materials with a potassium-to-magnesium ratio of 4.0 or larger show wide decomposition peaks on the DSC curves and lower onset and peak-minimum temperatures. Materials with a potassium-to-magnesium ratio of below 4.0 show a more narrow peak that occurs at higher temperatures and this is true regardless of the reagents used or whether the reaction stoichiometry is limited or complete.

Figure 4:
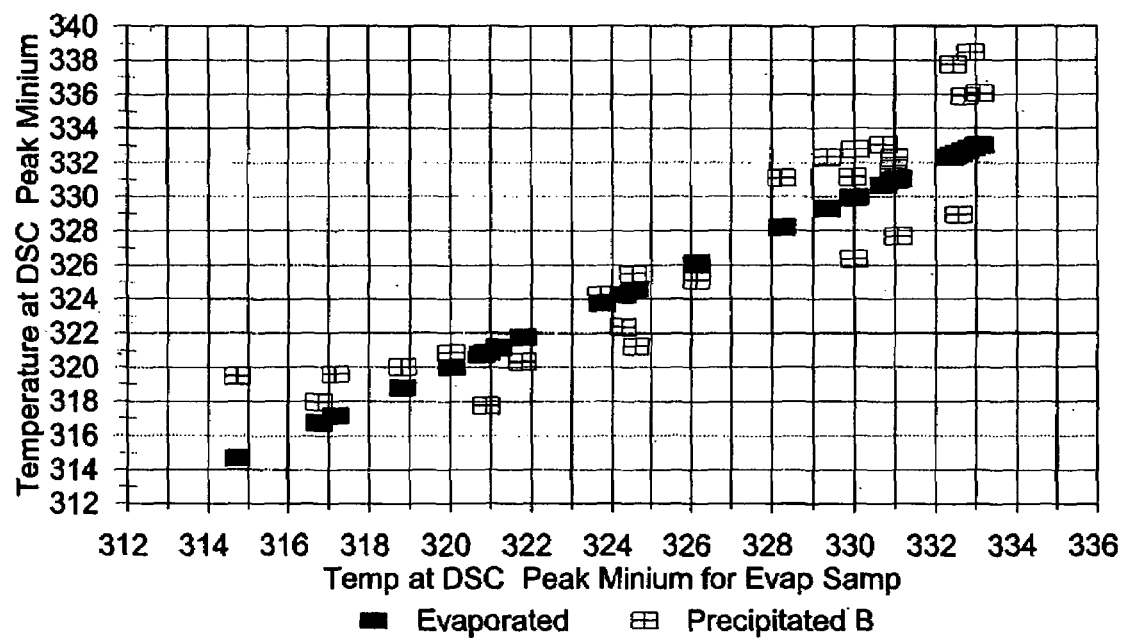
FIG. 4. DSC peak minima data for precipitated versus evaporated samples.
Figure 5:
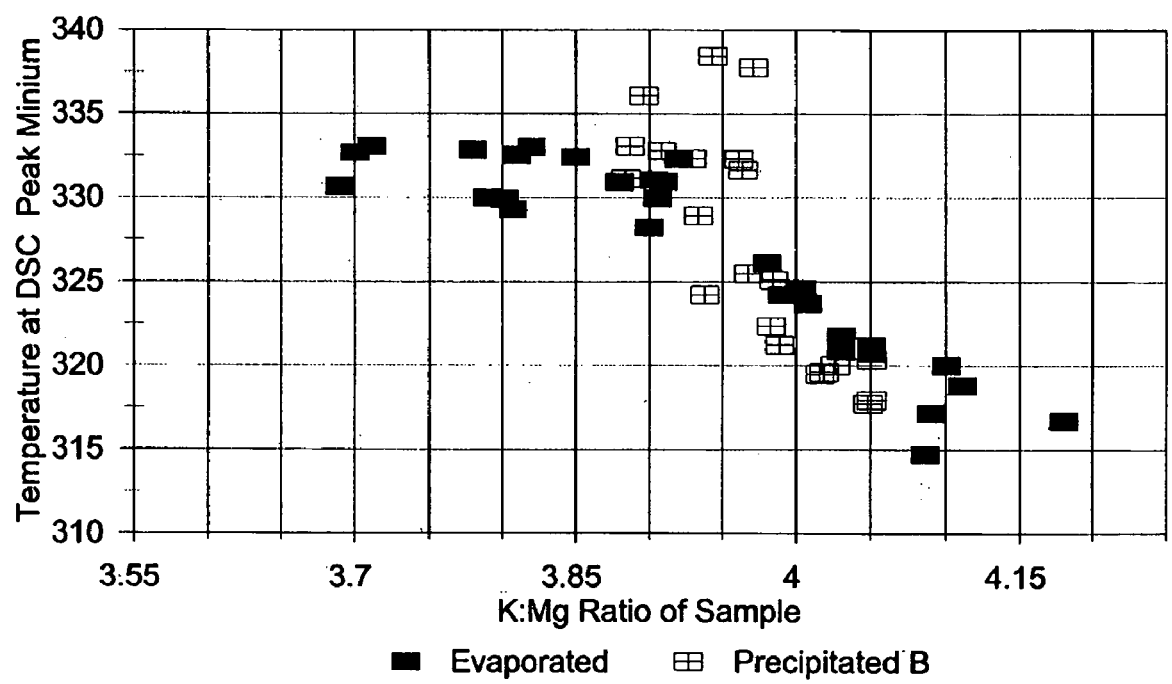
FIG. 5. DSC peak minima data for precipitated versus evaporated samples.
Figure 6:
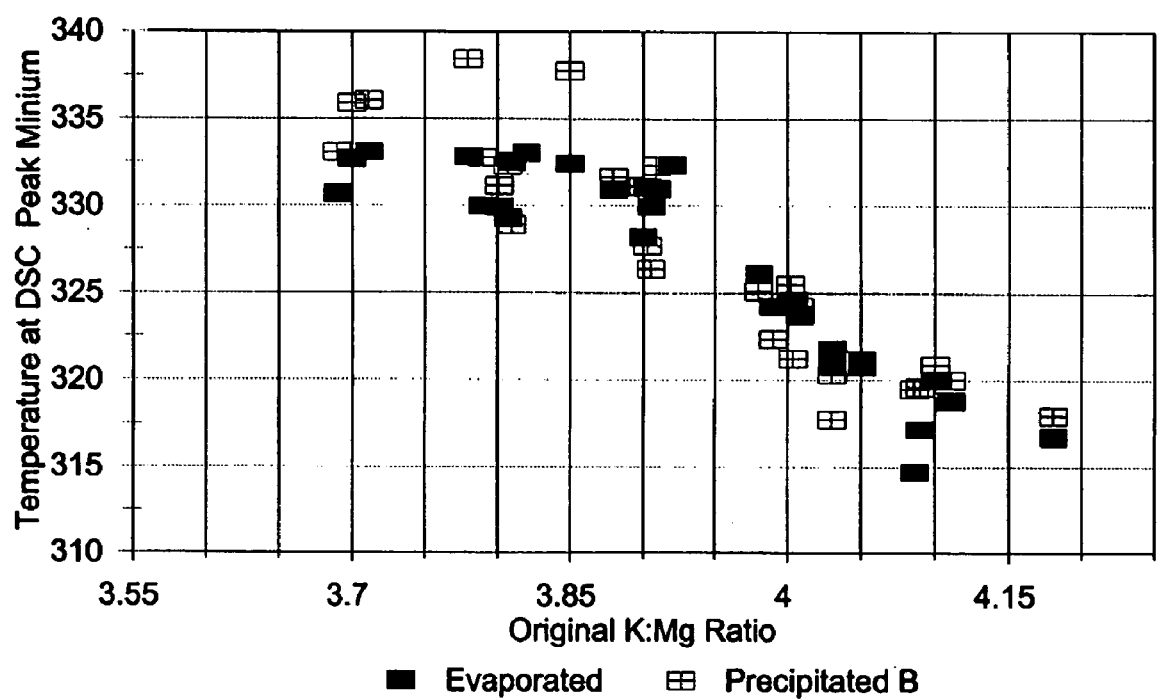
FIG. 6. DSC peak minima as a function of original K:Mg ratio for PMC.

Examining the DSC data for both evaporated and precipitated samples shows little difference in the DSC curves in spite of the difference in the potassium-to-magnesium ratio. This is illustrated by the modulated DSC data shown in FIGS. 4–6. FIG. 4 shows that there is little difference between the peak minima for precipitated versus evaporated samples. FIG. 5 shows the peak minima plotted as a function of the potassium-to-magnesium ratio as determined by assay for the individual samples. FIG. 6 shows the peak minima plotted as function of the original potassium-to-magnesium ratio as formulated. Note that the DSC data and consequently the structure of the material correlate with the starting ratio, rather than the actual ratio.

Figure 7:
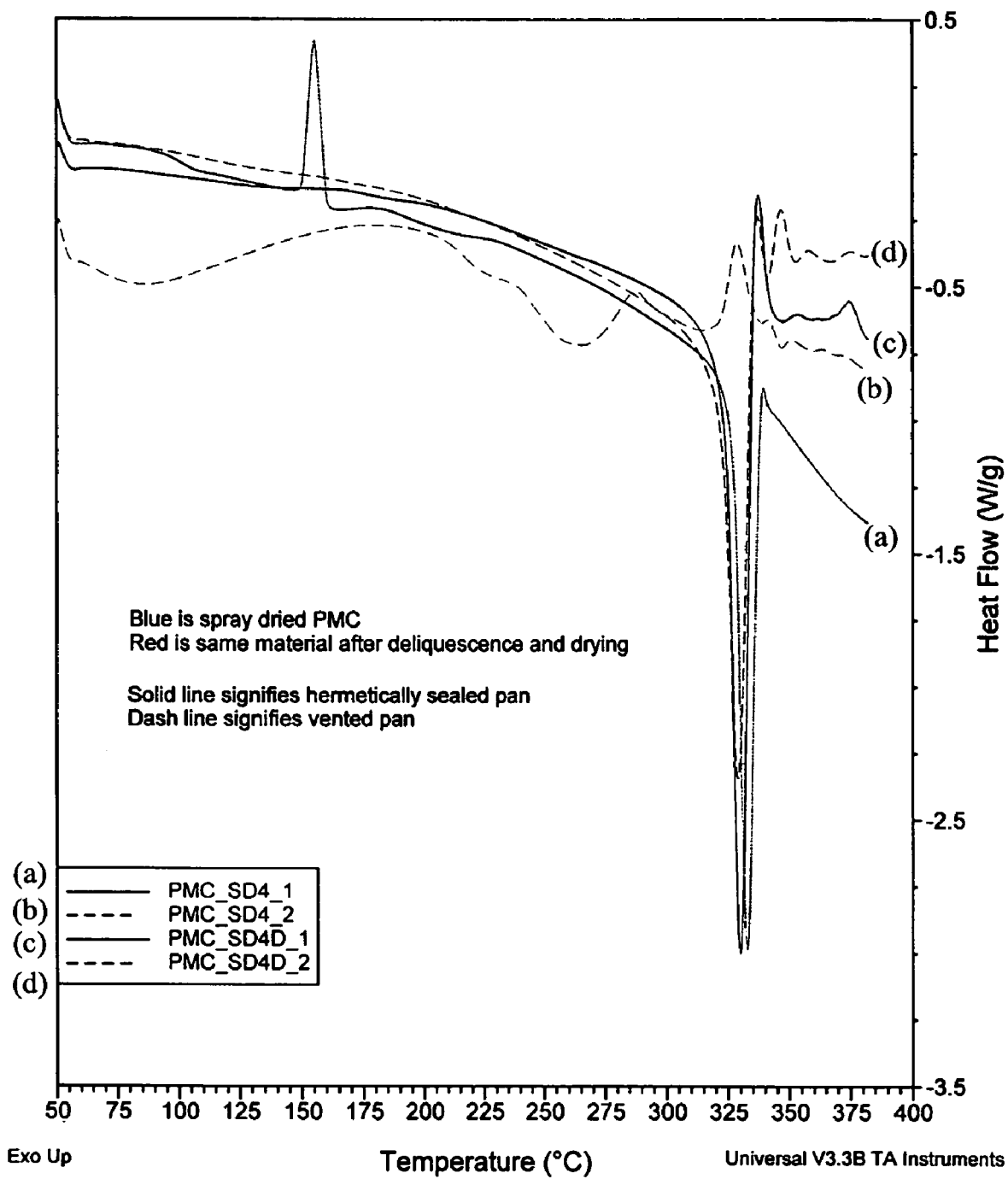
FIG. 7. DSC curves for spray-dried material for PMC.

As mentioned above, spray-dried PMC has been produced that is very different from oven-dried or room temperature dried PMC. The DSC of this spray-dried material varies with the type of DSC pan. The thermogram depends on whether the sample was placed in a hermetically-sealed pan or in a pan vented to atmospheric pressure. FIG. 7 shows the modulated DSC curves for the spray-dried material in a hermetically-sealed pan and in a vented pan. It also shows the curves for spray-dried material that was exposed to humidity and had deliquesced and dried. The spray-dried sample placed in a vented pan decomposed at a much lower temperature and with a broader decomposition peak compared to the sample dried in an oven or at room temperature. However, a spray-dried sample placed in a hermetically-sealed pan shows a DSC curve with an irreversible exothermic peak, followed by essentially the same high temperature decomposition peak seen for oven-dried material. Spray-dried PMC exposed to room humidity and left overnight on a watch glass changes forms. The fine powder coalesced into little circles or semi-spheres. These circles were collected and ground and the DSC thermogram obtained. The curve for the "changed" spray-dried PMC was the same as for oven-dried PMC. It showed no early decomposition in a vented pan and showed no exothermic peak in a hermetically-sealed pan.

These data are consistent with the formation of a metastable form of PMC upon spray drying. This form decomposes more easily than the oven-dried PMC. When the DSC is run using a hermetically-sealed sample pan, the metastable form does not decompose but undergoes an exothermic phase transformation to the same form as the oven-dried material. When exposed to humidity, the metastable form deliquesces and then redries to the stable oven-dried form.

Spray drying appears to be a very convenient way to dry the material. One skilled in the art recognizes that the various spraying methods can be adjusted to control the process to favor the formation to the more stable form or to convert the spray-dried material into the stable form more easily than drying slowly.

Enhanced Thermal Stability of the Composition

Analytical experiments have confirmed the enhanced thermal stability of the new composition of potassium magnesium citrate of the present invention in comparison to the prior art composition. Experimental batches of the composition made under widely varying mixing conditions. The batches were made varying the potassium to magnesium mole ratio from about 3.95 to about 4.20. Differential Scanning Calorimetry (DSC) experiments demonstrate a shift in temperature of the DSC minimum.

Figure 8:
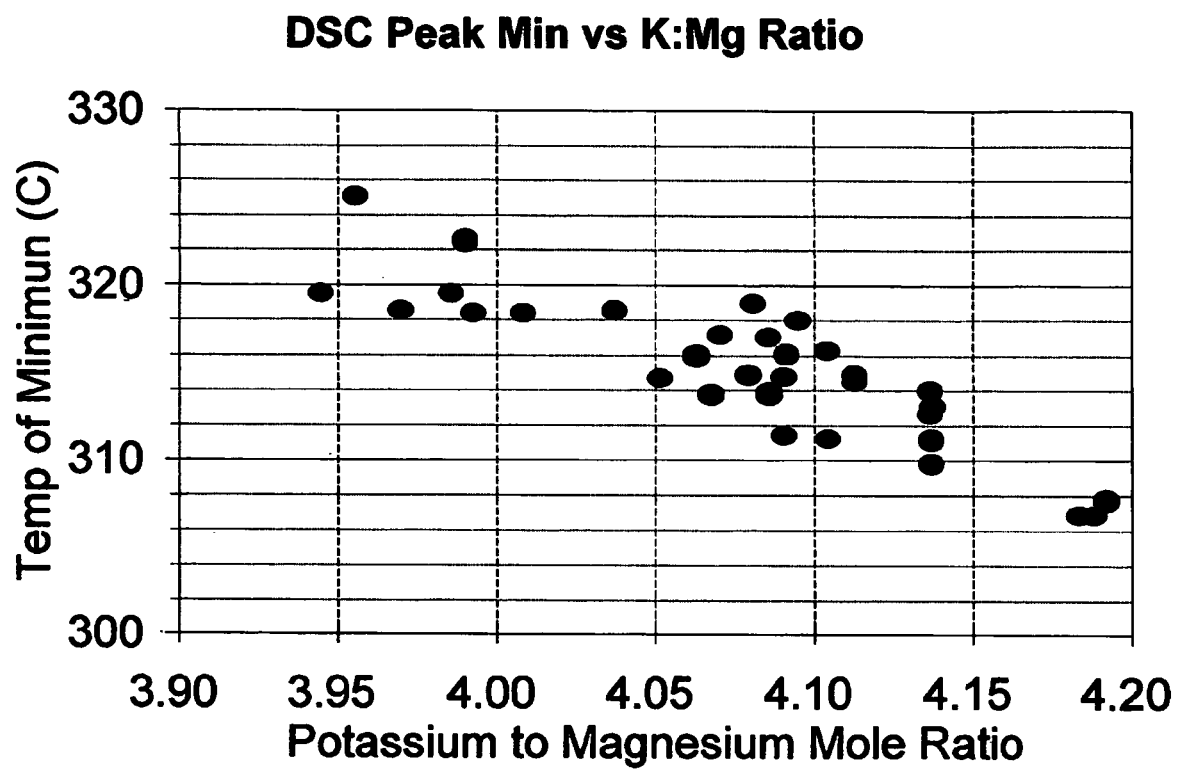
FIG. 8. DSC peak minima versus K:Mg ratio for PMC.
Figure 9:
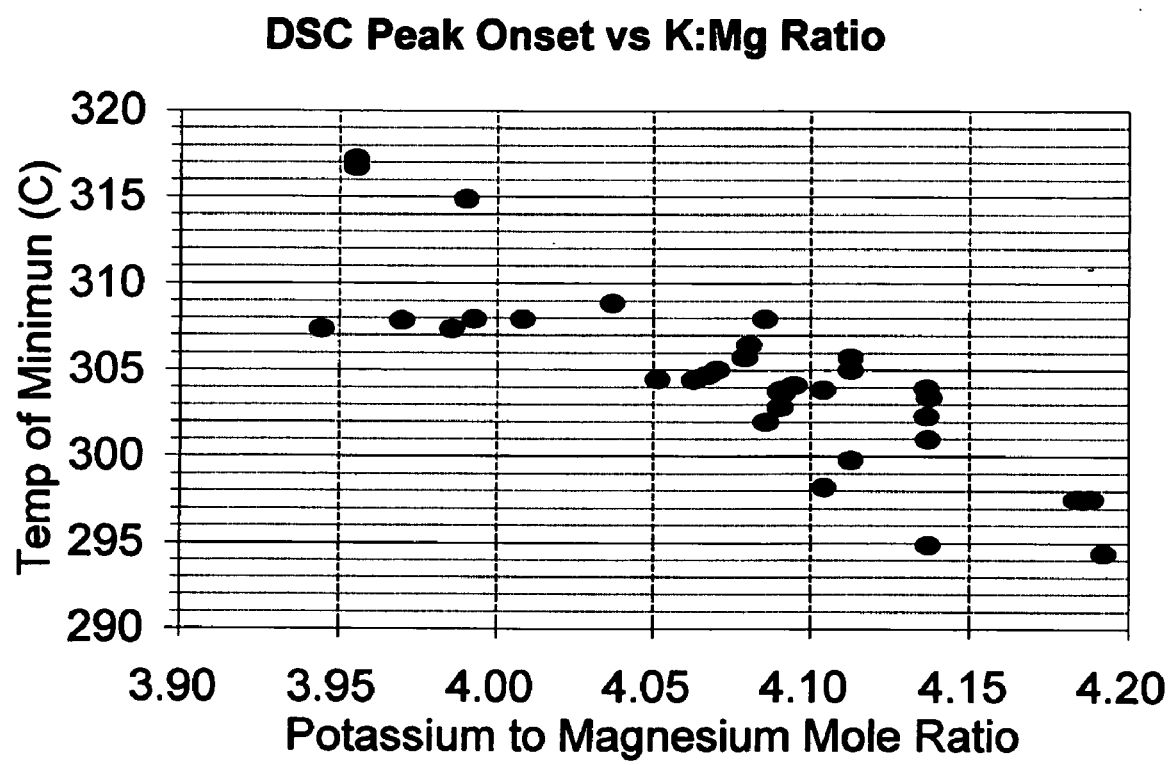
FIG. 9. DSC peak onset versus K:Mg ratio for PMC.

The temperature of the DSC peak minimum was observed as the potassium:magnesium mole ratio of the composition was varied. Modulated DSC results are shown in FIG. 8. As the potassium:magnesium mole ratio is increased from approximately 3.95 to about 4.20, the temperature of the DSC minimum shifts to lower temperatures, indicative of a lower temperature phase transition. Compositions of K:Mg mole ratios of less that 4 demonstrate greater thermal stability than do those having K:Mg mole ratios of 4 or greater. In FIG. 9, the modulated DSC peak onset temperature is plotted versus the K:Mg mole ratio. As the K:Mg mole ratio increases, the DSC peak onset shifts to lower temperature, indicative of an earlier phase transition and lowered thermal stability of the salt. The data shown in FIGS. 8 and 9 were obtained from pilot scale batches using different mixing conditions.

Figure 10:
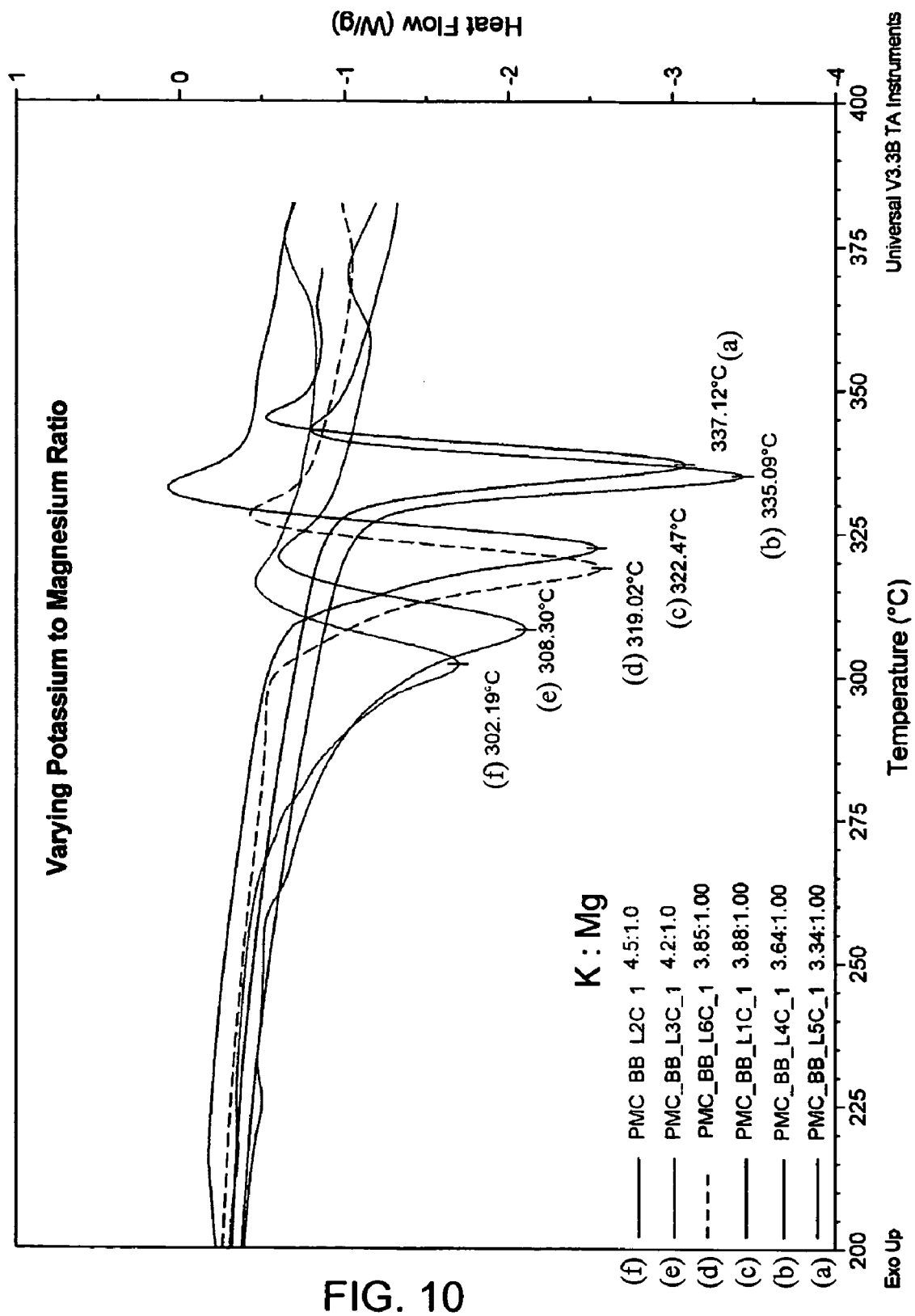
FIG. 10. DSC curves for PMC as K:Mg ratio is varied.
Figure 11:
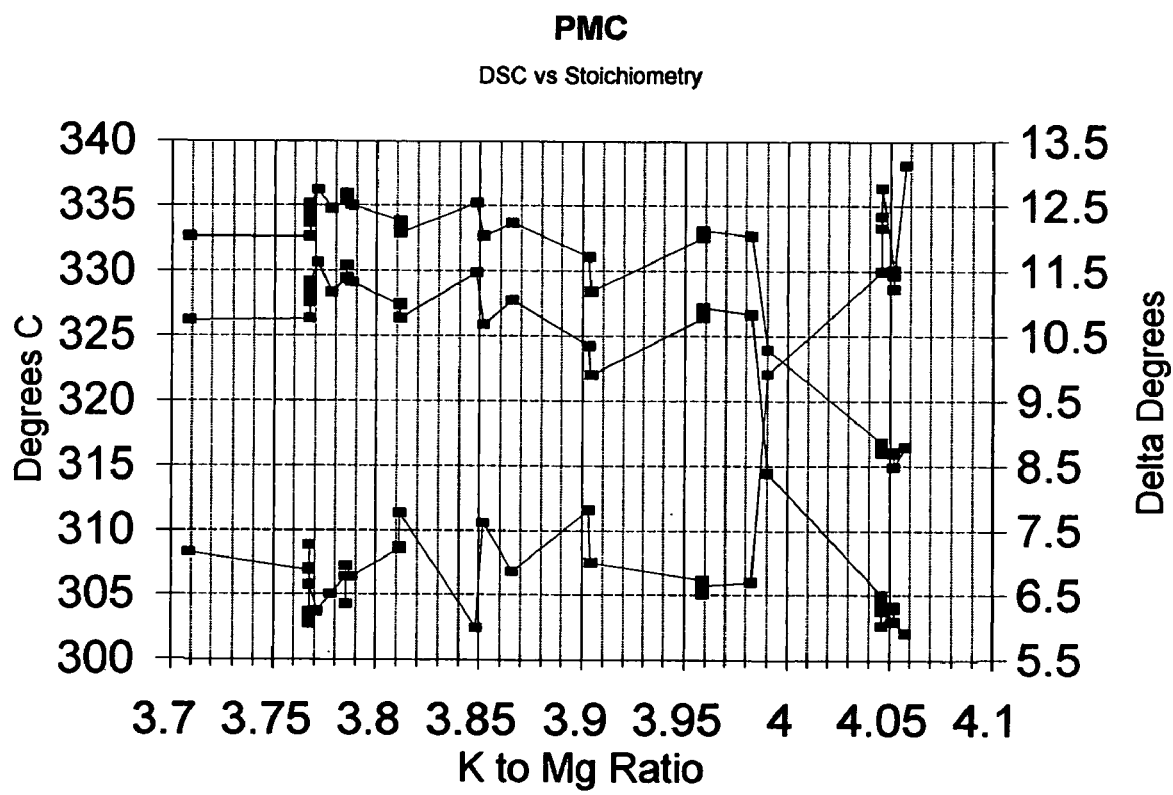
FIG. 11. DSC temperature versus stoichiometry (K:Mg ratio) for PMC.

Beaker size batches of PMC were made with the intent that only the potassium:magnesium ratio would vary, leaving no unreacted citric acid or carbonate in the final product. The trend is clear and is consistent with that described above. FIG. 10 demonstrates that as the K:Mg ratio is decreased, the modulated DSC peak minimum and onset temperatures shift to higher temperatures. The modulated DSC data of FIG. 11 demonstrates the behavior of DSC peak minimum, DSC peak onset temperature, and DSC peak width (indicated as Delta Degrees). The curves cross over at a K:Mg ratio of approximately 4, indicative of a transition between compositions.

Figure 12:
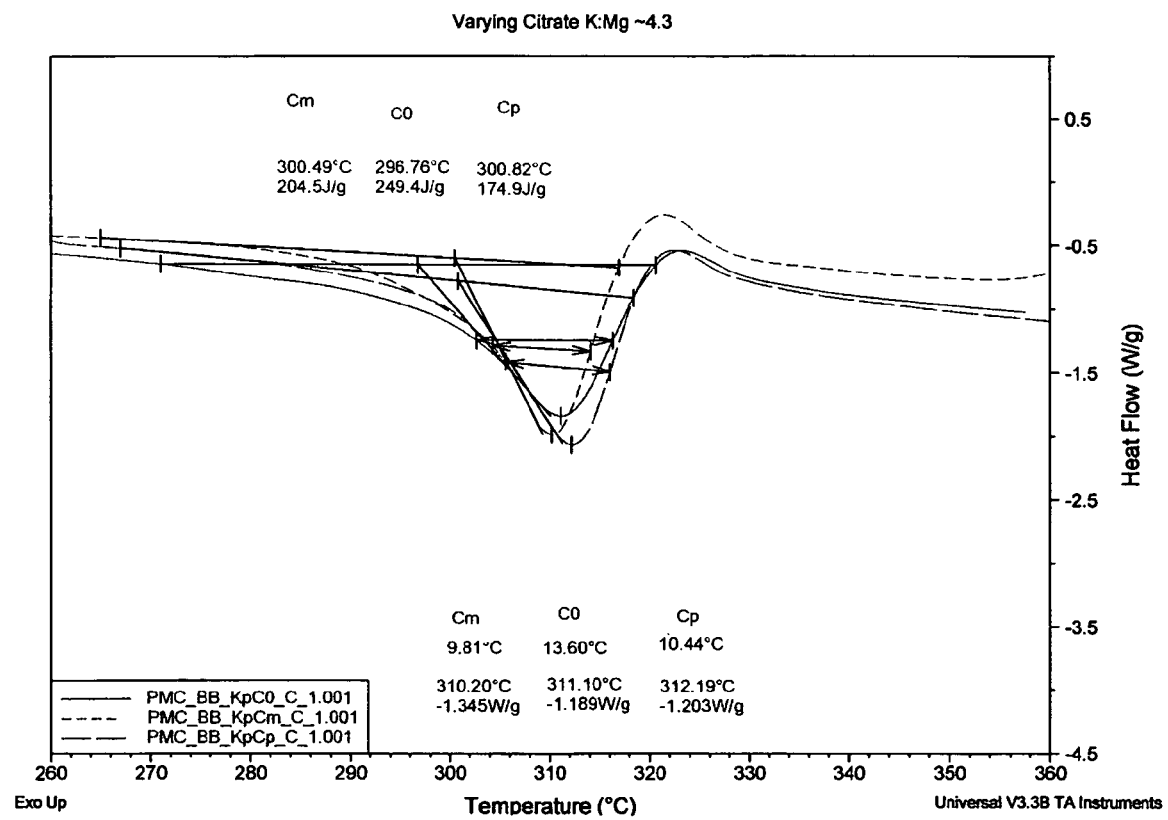
FIG. 12. Effect of citric acid on DSC curves for PMC for K:Mg of ca. 4.3.
Figure 13:
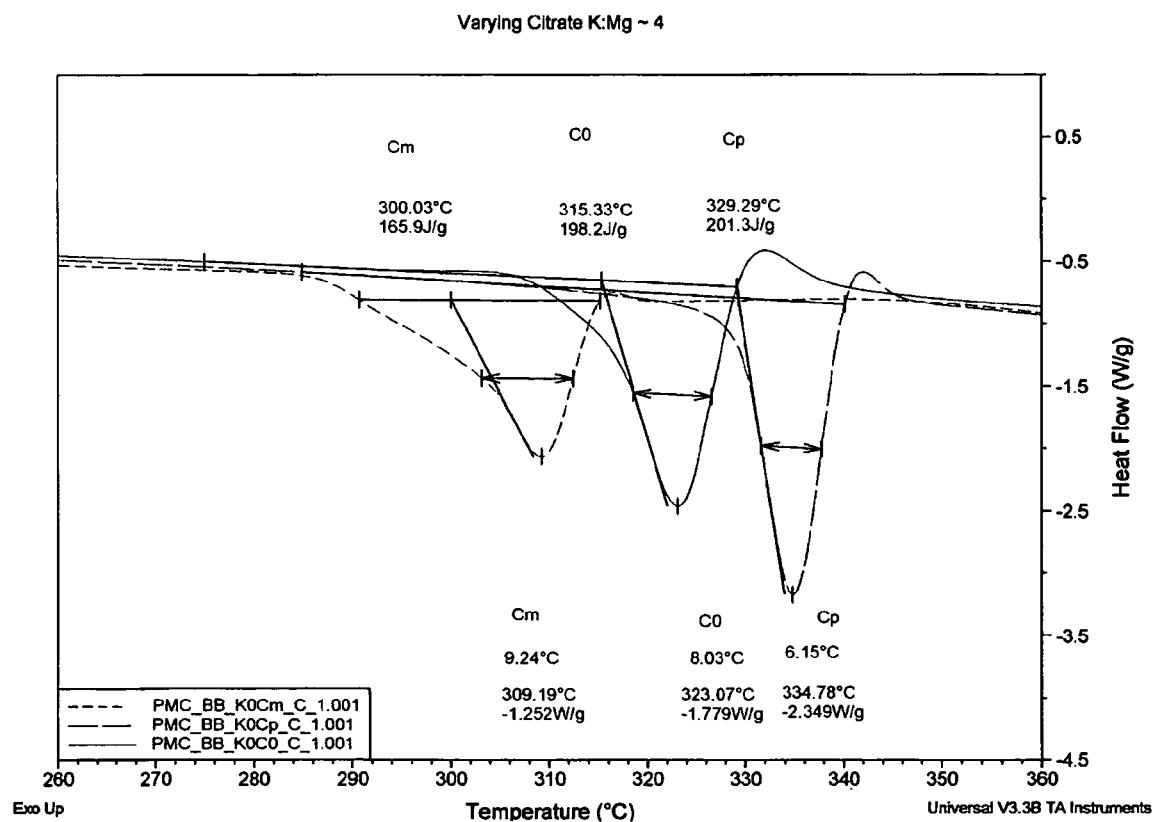
FIG. 13. Effect of citric acid on DSC curves for PMC for K:Mg of ca. 4.
Figure 14:
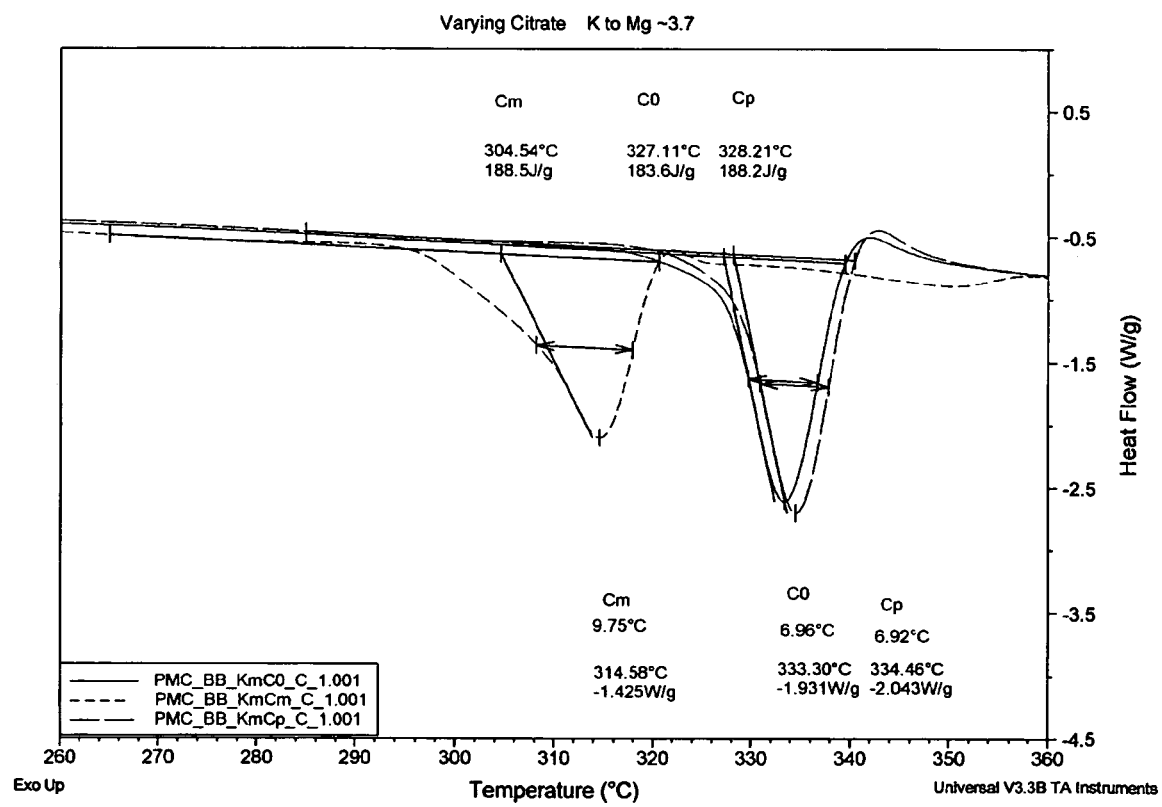
FIG. 14. Effect of citric acid on DSC curves for PMC for K:Mg of ca. 3.7.

FIGS. 12, 13, and 14 demonstrate the effect of citric acid on the formation of the composition of the present invention. As can be seen, the presence of excess citric acid tends to promote the formation of the thermally stable composition of the present invention, characterized by higher DSC peak minimum temperatures, sharper DSC curves as measured by peak width, and higher DSC onset temperatures. Although not intending to be bound by theory, the excess citric acid is believed to neutralize any basic impurities such as hydroxide and carbonate salts.

Analytical Characterization of the Composition

A number of tests were performed to demonstrate that the material of the present invention exhibiting enhanced thermal stability is a new form of PMC and not merely a blend of potassium citrate ($K_3C_6H_8O_7$) and magnesium citrate ($Mg_3(C_6H_8O_7)_2$).

Analytical $^{13}C$ nuclear magnetic resonance spectroscopy ($^{13}C$-NMR) was used to compare spectral response of the composition of the present invention to potassium citrate, magnesium citrate, and a dry stoichiometric blend of potassium citrate and magnesium citrate. The data demonstrates definitive chemical shifts in the spectrum of PMC compared to potassium citrate, magnesium citrate, and a dry stoichiometric blend of potassium citrate and magnesium citrate while the spectrum of the dry blend can be resolved as the simple addition of the spectral components of the individual blend components.

The distinction between the individual potassium and magnesium citrate salts, the blend of the two salts and the new composition is further demonstrated using Fourier-Transform Infrared Spectroscopy (FT-IR). The spectrum of PMC was compared to those of potassium citrate and magnesium citrate. Bands unique to the composition of the present invention are indicated at 1141.60, 949.86, and 919.83 wavenumbers. The FT-IR spectrum of the composition of the present invention was compared to the stoichiometric blend. Bands unique to the composition of the present invention are indicated at 1268.53, 1203.44, 1139.91, 952.41, 935.37, and 919.87 wavenumbers. The spectrum of the new composition shows bands that are not present in either the spectrum of potassium citrate or magnesium citrate. In addition, spectral lines present in the spectra of potassium citrate and magnesium citrate are missing from the spectrum of PMC. These differences are clear indicators of a different chemical structure of the composition of the present invention relative to both the individual potassium and magnesium citrate slats and to the blend.

Raman spectra of the composition of the present invention and a blend of potassium citrate and magnesium citrate also demonstrate the unique chemical nature of the composition of the present invention. The Raman spectra of the composition of the present invention was compared to the stoichiometric blend of potassium citrate and magnesium citrate. Spectral lines present in the spectra of potassium citrate and magnesium citrate are missing from the spectrum of the composition of the present invention. This is particularly significant in the phonon region (approximately 150 to 750 $cm^{-1}$). The reduced number of Raman bands in the phonon region indicates a crystallographically unique structure containing symmetry elements of higher order than either the individual salts or the dry blend.

X-ray powder diffraction patterns were measured for potassium citrate, magnesium citrate, the blend of potassium citrate and magnesium citrate, and the composition of the present invention. The defined pattern for the composition of the present invention does not include the diffraction pattern from potassium citrate or magnesium citrate. Notably, the peak seen at $2\theta=22.9°$ is the 100% intensity peak for the new composition and this peak could not be matched by any known, catalogued compound containing magnesium, potassium, or citrate.

NIR data was acquired for the composition of the present invention, potassium citrate, magnesium citrate, and the stoichiometric blend of potassium citrate and magnesium citrate. As was found using the previously discussed analytical techniques, the spectrum for the composition of the present invention does not match that of the stoichiometric blend. The magnitude of the differences between the spectra was examined by comparing the NIR spectra of 6 batches of the composition of the present invention. The correlation coefficient for the same average spectrum for the composition of the present invention compared to spectrum of a dry stoichiometric blend of potassium citrate and magnesium citrate was calculated. The correlation coefficient for the blend was 0.1659 compared to a correlation coefficient of 0.999 for each of the batches of the composition of the present invention.

One of the most impressive differences between the composition of the present invention and that of potassium citrate, magnesium citrate and a dry stoichiometric blend is the thermal stability as demonstrated by Modulated Differential Scanning Calorimetry (MDSC). From the MDSC data, it can be seen that for the composition of the present invention, the onset of decomposition is at approximately 310° C. and 260° C. for the stoichiometric dry blend of potassium citrate and magnesium citrate. The onset of decomposition occurs at 260° C. for potassium citrate and 250° C. for magnesium citrate taken alone. The higher thermal stability demonstrates that the composition of the present invention is chemically and physically distinct from potassium citrate, magnesium citrate, or a blend. It implies that the chemical bonds for the composition of the present invention are more stable than those for either potassium citrate or magnesium citrate, further supporting a distinct composition.

The composition of the present invention is crystalline and the structure is of higher symmetry than potassium citrate or magnesium citrate. A blend would not be expected to increase symmetry. The composition of the present invention is has greater thermal stability than potassium citrate or magnesium citrate. The composition of the present invention is unique both spectroscopically and crystallographically and can be reproducibly made. The data confirms that the composition of the present invention is a chemical compound having an empirical formula of very close to that of tetra-potassium magnesium dicitrate, or $K_4Mg(C_6H_5O_7)_2$, and an empirical formula weight of 558.91 g/mol. This composition provides a unique source of potassium ions, magnesium ions, and citrate ions for one chemical compound.

The data from the precipitation studies demonstrate that a new chemical compound of PMC has been formed. There are two compounds of PMC, closely related. PMC1 (an arbitrary designation hereinafter indicating the PMC of the prior art) is a compound made with a potassium-to-magnesium ratio of 4.0 or slightly greater. It is characterized by DSC as having a lower and broader decomposition curve than the PMC of the present invention (hereinafter "PMC2" in order to distinguish it from the prior art "PMC1"). PMC2 decomposes at a higher temperature and the decomposition peak in DSC is narrow. It forms with a stoichiometry of just less than 4.0.

The PMC2 that is formed by spray drying is clearly a metastable form. Material having a potassium-to-magnesium ratio less than 4.0 has been spray-dried and the spray-dried material appears to be a polymorph of PMC2. Spray drying is possible when the salt product is completely dissolved in the reaction mixture; a condition that occurs when the water content of the reaction mixture is at least 120% by weight relative to theoretical dry yield of potassium magnesium citrate. This polymorph has an endothermic peak for decomposition from the modulated differential scanning calorimetry thermogram comprising an onset temperature of greater than 320° C., a peak minimum temperature of greater than 327° C.; and, a peak width of less than 9° C.

Figure 15:
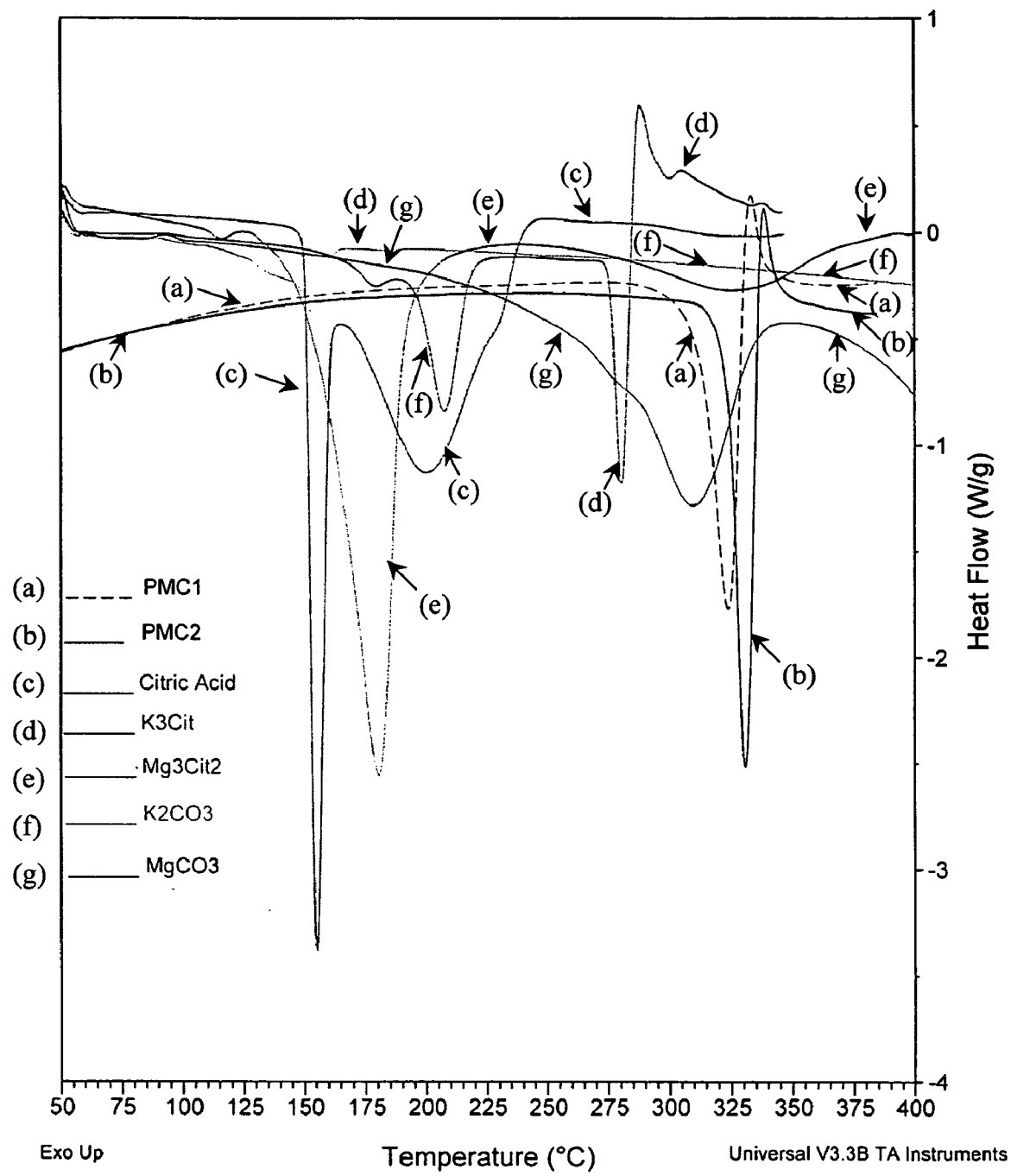
FIG. 15. DSC curves for PMC1 and PMC2 and related compounds.
Figure 16:
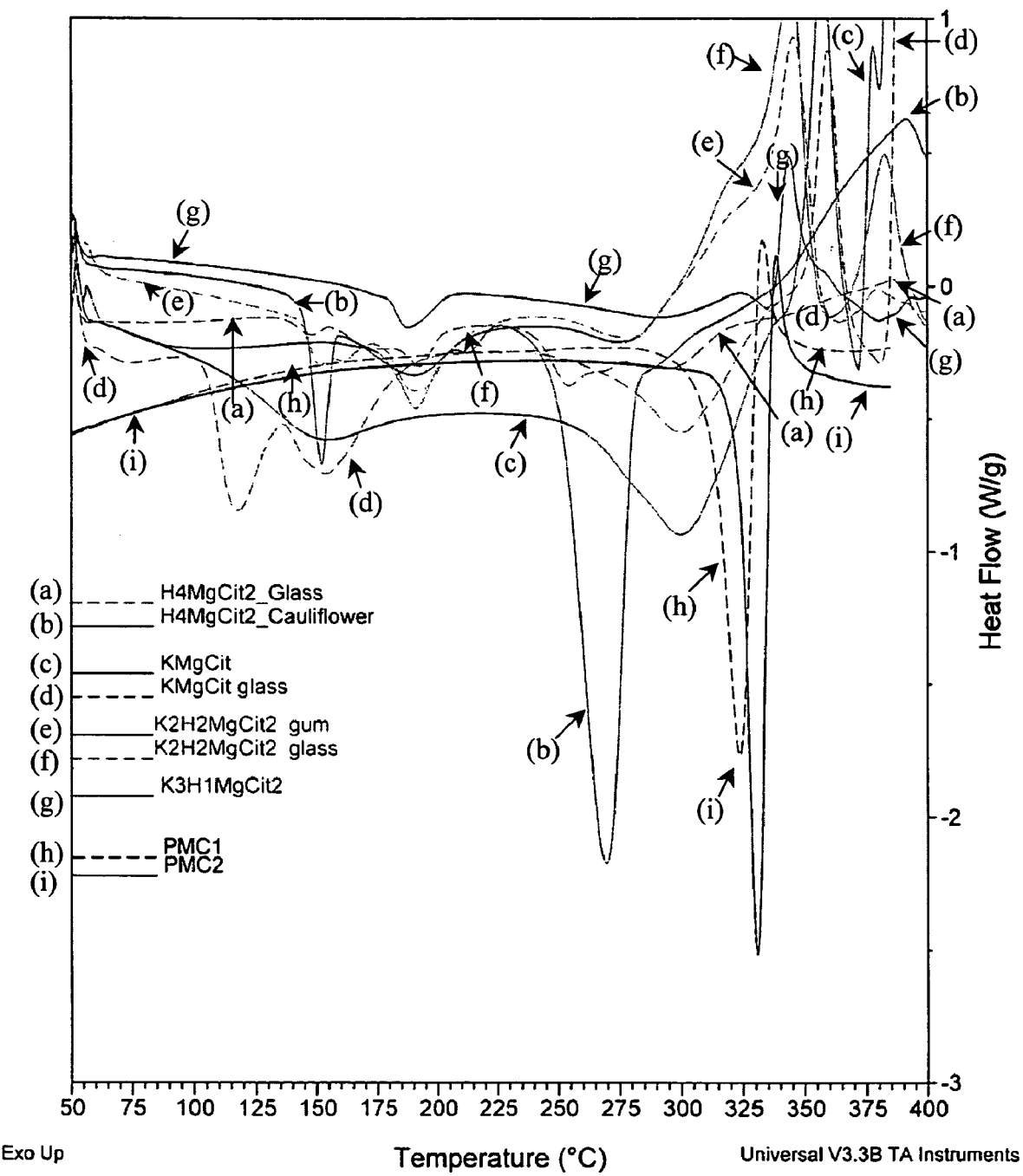
FIG. 16. DSC curves for PMC1 and PMC2 and related compounds.

FIGS. 15 and 16 compare the DSC curves of both PMC1 and PMC2 to those of other related compounds. For each PMC compound, the decomposition curve is easily distinguishable from these related compounds and from each other. The large difference in the DSC cures of related materials shows the uniqueness of PMC1 and PMC2. Neither of the compounds is a simple mixture of potassium magnesium citrate.

The new compound may be tableted with or without other components (such as excipients, lubricants, etc.) to make a dietary supplement. Other dosage forms, both oral and non-oral are possible. Of the two compounds, PMC2 has advantages for use in the dosage form. Because it is more thermodynamically stable, it will be easier to use the DSC curves to test for purity and adulteration. Using the appropriate stoichiometry, it not harder to manufacture than PMC1. It appears from the data that a potassium-to-magnesium ratio of 3.9 is sufficiently lower than 4.0 to assure that PMC made by a complete reaction and then dried will have the thermal properties of PMC2. This would correspond to a composition of $K_{3.967}Mg_{1.017}(C_6H_5O_7)_2$. The final stoichiometry for the reaction could be find-tuned as production processes are fine-tuned.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A composition comprising a salt of potassium, magnesium, and citrate having the general formula $K_xMg_y(C_6H_5O_7)_z$, wherein z is 2, and x is greater than or equal to 3.7 and less than or equal to 3.95 and y is greater than or equal to 1.0 and less than 1.15, and wherein electroneutrality is preserved by:
    adjusting x and y so that x+2y is equal to 6; or,
    including ions other than potassium, magnesium, or citrate.

2. The composition of claim 1 wherein said ions other than potassium, magnesium, or citrate are hydrogen ions.

3. The composition of claim 1 wherein x is greater than or equal to 3.8 and less than or equal to 3.95.

4. The composition of claim 1 wherein for the salt, the endothermic peak for decomposition from the modulated differential scanning calorimetry thermogram comprises:
    an onset temperature of greater than 320° C.;
    a peak minimum temperature of greater than 327° C.; and,
    a peak width of less than 9° C.

5. A pharmaceutical composition useful as a magnesium and potassium dietary supplement, said composition comprising magnesium potassium citrate as a single salt, said salt having the general formula $K_xMg_y(C_6H_5O_7)_z$, wherein z is 2, and x is greater than or equal to 3.7 and less than or equal to 3.95 and y is greater than or equal to 1.0 and less than 1.15, and wherein electroneutrality is preserved by:
    adjusting x and y so that x+2y is equal to 6; or,
    including ions other than potassium, magnesium, or citrate.

6. The composition of claim 5 wherein said ions other than potassium, magnesium, or citrate are hydrogen ions.

7. The composition of claim 5 wherein said ratio of potassium ion to magnesium ion is less than or equal to 3.95:1 and greater than or equal to 3.8:1.

8. The composition of claim 5 wherein for the salt, the endothermic peak for decomposition from the modulated differential scanning calorimetry thermogram comprises:
    an onset temperature of greater than 320° C.;
    a peak minimum temperature of greater than 327° C.; and,
    a peak width of less than 9° C.

9. A method for producing a magnesium potassium citrate composition comprising the steps of:
    mixing citric acid and water with uninterrupted agitation;
    while still agitating, gradually adding a magnesium compound and a potassium compound thereto in such proportions that the mixture thus formed comprises potassium ions, magnesium ions, and citrate ions and has the general formula $K_xMg_y(C_6H_5O_7)_z$, wherein z is 2, and x is greater than or equal to 3.7 and less than or equal to 3.95 and y is greater than or equal to 1.0 and less than 1.15, and wherein electroneutrality is preserved by:
    adjusting x and y so that x+2y is equal to 6; or,
    including ions other than potassium, magnesium, or citrate;
    blending the resultant composition; and thereafter,
    drying and milling the resultant composition to form a magnesium potassium citrate composition.

10. The method of claim 9 wherein the water content of the reaction mixture is at least 120% by weight relative to theoretical dry yield of potassium magnesium citrate.

11. The method of claim 10 wherein said step of drying comprises spray drying.

12. The method of claim 11 further comprising the step of exposing the reaction mixture to heat, pressure, humidity, or any combination thereof.

13. The method of claim 9 wherein the water content of the reaction mixture is about 50% by weight relative to theoretical dry yield of potassium magnesium citrate.

14. The method of claim 9 wherein said magnesium compound is selected from the group consisting of magnesium carbonate, magnesium citrate, magnesium oxide, and magnesium hydroxide.

15. The method of claim 9 wherein said potassium compound is selected from the group consisting of potassium carbonate, potassium citrate, potassium bicarbonate, and potassium hydroxide.

16. The method of claim 9 wherein the composition has an endothermic peak for decomposition in its modulated differential scanning calorimetry thermogram, said peak comprising an onset temperature of greater than 320° C.; a peak minimum temperature of greater than 327° C.; and a peak width of less than 9° C.

17. A method for supplementing dietary potassium and magnesium comprising administering to a person or animal, potassium magnesium citrate in a single salt consisting essentially of potassium, magnesium and citrate ions and has the general formula $K_xMg_y(C_6H_5O_7)_z$, wherein z is 2, and x is greater than or equal to 3.7 and less than or equal to 3.95 and y is greater than or equal to 1.0 and less than 1.15, and wherein electroneutrality is preserved by:
adjusting x and y so that x+2y is equal to 6; or,
including ions other than potassium, magnesium, or citrate.

18. The method of claim 17 wherein said step of administering comprises orally administering.

19. The method of claim 17 wherein said step of orally administering comprises orally administering tablets.

20. The method of claim 17 wherein said salt has an endothermic peak for decomposition in its modulated differential scanning calorimetry thermogram, said peak comprising an onset temperature of greater than 320° C.; a peak minimum temperature of greater than 327° C.; and a peak width of less than 9° C.

* * * * *